United States Patent [19]

Heilen et al.

[11] 4,374,274

[45] Feb. 15, 1983

[54] PREPARATION OF α-METHYLSUBSTITUTED CARBONYL COMPOUNDS

[75] Inventors: Gerd Heilen, Speyer; Klaus Halbritter, Mannheim; Walter Gramlich, Edingen, all of Fed. Rep. of Germany

[73] Assignee: BASF Aktiengesellschaft, Ludwigshafen, Fed. Rep. of Germany

[21] Appl. No.: 186,130

[22] Filed: Sep. 11, 1980

[51] Int. Cl.³ .............................................. C07C 45/45
[52] U.S. Cl. .................................. 568/313; 568/345; 568/390
[58] Field of Search ................ 568/313, 345, 390, 391

[56] References Cited

U.S. PATENT DOCUMENTS 2,288,306  6/1942  Wagner ................................ 568/390
3,410,909  11/1968 Fleischer et al. .
3,542,878  11/1970 Swift ................................... 568/313
3,932,518  1/1976  Arpe .
4,146,581  3/1979  Nissen et al. ........................ 568/313
4,210,767  7/1980  Yashida et al. ...................... 568/816

FOREIGN PATENT DOCUMENTS 1227708  4/1971  United Kingdom ................ 568/390

Primary Examiner—James H. Reamer
Attorney, Agent, or Firm—Oblon, Fisher, Spivak, McClelland & Maier

[57] ABSTRACT

A process for the preparation of α-methylsubstituted ketones by reacting the corresponding non-methylsubstituted ketones with formaldehyde under hydrogenating conditions. The reaction proceeds easily and with good yields if a catalyst containing metallic palladium deposited on a zirconium, hafnium, titanium or tin phosphate is used. The products are valuable intermediates for the preparation of dyes, crop protection agents or drugs.

9 Claims, No Drawings

PREPARATION OF α-METHYLSUBSTITUTED CARBONYL COMPOUNDS

The present invention relates to a process for the preparation of α-methylsubstituted ketones by reacting the corresponding non-methylsubstituted ketones with formaldehyde under hydrogenating conditions.

The introduction of methyl groups in the α-position to a carbonyl group is known per se. For example, Houben-Weyl, Methoden der organischen Chemie, Volume VII, 2b, page 1385 et seq. describes the alkylation of carbonyl compounds by reaction with alkyl halides, preferably with the bromides or iodides. Disadvantages of this method are that alkyl halides, which are relatively expensive, are used as starting compounds and that alkaline substances which can often only be employed in combination with expensive solvents, such as an alkali metal amide in liquid $NH_3$, are used, mostly in stoichiometric amounts.

A further conventional method is to carry out an aldol condensation of the carbonyl compound with formaldehyde, dehydrate the aldol adduct formed and then hydrogenate the resulting $\alpha,\beta$-unsaturated carbonyl compound to give the desired end product. It is true that the formaldehyde used is a cheap starting material but the reaction must be carried out in two or three separate steps, in different apparatuses.

A single-step alkylation, wherein a ketone is reacted with methanol over a copper or silver catalyst to give the corresponding α-methylsubstituted ketone is described in German Patent 2,257,675. Disadvantages of this process are that dialkylated and/or polyalkylated compounds are also formed, and that in some cases the yields are rather poor. For example, when reacting methyl ethyl ketone with methanol, the product contains not only methyl isopropyl ketone but also similar amounts of ethyl isopropyl ketone and diethyl ketone. Furthermore, even a certain proportion of diisopropyl ketone is formed.

Further, German Published Application DAS No. 1,922,755 discloses the self-condensation of ketones to give novel ketones having twice the number of carbon atoms, for example the preparation of methyl isobutyl ketone from acetone. The catalyst used is a Zr, Hf, Ti or Sn phosphate, additionally containing small amounts of palladium.

We have found, surprisingly, that these catalysts are also useful in the reaction of carbonyl compounds with formaldehyde. This was unexpected since it had to be assumed that on using these catalysts a self-condensation of the particular carbonyl compound would occur preferentially. Instead, we have found that when a mixed condensation, i.e. a condensation of a carbonyl compound with formaldehyde, is carried out over such a catalyst, the self-condensation occurs to only a negligible extent even if a large excess of the carbonyl compound is employed.

Accordingly, the invention relates to a process for the preparation of a carbonyl compound of the general formula I

where $R^1$ and $R^2$ are straight-chain or branched alkyl of 1 to 8, preferably 1 to 4, carbon atoms or are aryl or aralkyl, $R^1$ may also be H and $R^1$ and $R^2$ together with the carbon atoms between them may also be members of an alicyclic ring, wherein a ketone of the general formula II

is reacted with formaldehyde at 50°–230° C. in the presence of hydrogen and of a catalyst in which the active constituents are (a) a phosphate of one or more of the metals zirconium, titanium, hafnium and tin or a mixture of such phosphates and (b) metallic palladium deposited on this phosphate (or phosphate mixture).

The ketones of the formula II required as starting compounds are conventional commercial compounds. Examples include acetone, methyl ethyl ketone, diethyl ketone, cyclohexanone, acetophenone and 4-phenyl-butan-2-one.

The catalysts used in the novel process are disclosed in German Published Application DAS No. 1,922,755. They essentially consist of a phosphate of zirconium, hafnium, titanium or tin and additionally contain metallic palladium. There are no limits on the molar ration $PO_4^{3-}$: metal, but for reasons of economy metal phosphates in which the said ratio is from 3:1 to 1:3 are generally employed. Catalysts in which the molar ratio $PO_4^{3-}$: metal is from 0.6:1 to 1.7:1 are particularly advantageous. The amount of metallic palladium is not critical and is essentially decided by economic considerations. It is generally from 0.1 to 5.3% by weight, especially from 0.2 to 3.0% by weight, based on metal phosphate. The catalysts are prepared in a conventional manner as described in great detail in the above German Published Application, to which reference may be made. The catalyst may be employed as powder or as beads, pellets, tablets or granules.

The formaldehyde introduced into the reaction may be in a variety of forms. For example, it is possible to use paraformaldehyde dissolved or suspended in the carbonyl compound to be converted, or to employ commercial formaldehyde solutions, eg. a 30–40% strength solution of formaldehyde in water or in a lower alcohol.

The molar ratio of the carbonyl compound to be converted, of the formula II, to formaldehyde is not critical. Particularly good results are obtained if the carbonyl compound is used in excess. The molar ratio employed can vary from 1:1 to 20:1; preferably the molar ratio is from 1:1 to 15:1. An even higher excess in general offers no advantages and is therefore ruled out on economic grounds. It is noteworthy however that even with a higher excess of the carbonyl compound, self-condensation only occurs to a slight degree.

The novel process may be carried out continuously or batchwise. For continuous industrial operation, it is technologically advantageous to use a fixed catalyst bed in a reaction column and to pass the mixture together with hydrogen over the bed. For batchwise operation, it is advantageous to use the catalyst in suspension.

In principle the process may be carried out even at atmospheric pressure but in order to increase the reaction rate it is advantageous to operate under superatmospheric pressure, especially where low-boiling carbonyl compounds are employed. Usually, the hydrogen pressure is up to 100 bar; even higher pressures in general offer no advantages and are therefore uneconomical. Economically the most advantageous results are achieved at pressures of from 1 to 50 bar.

The reaction temperature used is advantageously from 50° to 230° C., preferably from 70° to 210° C. Below 50° C., the reaction rate drops substantially whilst above 230° C. there is a loss of yield due to continuing aldol condensations.

Where the carbonyl compound to be reacted is liquid, it is not necessary to use a solvent. Solid carbonyl compounds may be dissolved in any liquids which are inert under the reaction conditions, for example in paraffins, e.g. pentane, hexane and octane, cycloparaffins, e.g. cyclohexane, aromatics, eg. benzene and toluene, alcohols, e.g. methanol, ethanol and isopropanol, or esters, e.g. methyl acetate and ethyl acetate.

Using the novel process, α-methylsubstituted carbonyl compounds, which are mostly valuable intermediates for the preparation of dyes, crop protection agents or drugs, may be prepared in a technically simple and advantageous manner.

EXAMPLE 1

A catalyst which has been prepared as described in German Published Application DAS 1,922,755 (compare Table 1) by precipitating an aqueous solution of appropriate amounts of $ZrOCl_2.8H_2O$, $PdCl_2$ and $H_3PO_4$ by means of aqueous ammonia, followed by a reduction treatment, and which consists of zirconium phosphate with an added 0.5% by weight of metallic palladium was introduced, in the form of pills of diameter 3 mm, into a tubular reactor having a capacity of 1.8 liters and an internal diameter of 4.5 cm. 2.5 liters per hour of a mixture which consisted of 87.8% of methyl ethyl ketone and 12.2% of aqueous (30% strength by weight) formaldehyde solution were passed, at 180° C., through this tubular reactor, which was under a hydrogen pressure of 30 bar.

The reaction product obtained under these conditions was collected and subjected to fractional distillation; the fractions obtained were analyzed by gas chromatography. This indicated the following composition (neglecting the water employed and formed):

| | | |
|---|---|---|
| unconverted | 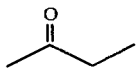 | 85.6% by weight |
| | 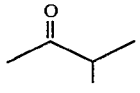 | 9.7% by weight |
| | 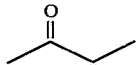 | 0.8% by weight |
| | 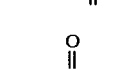 | 1.0% by weight |
| | 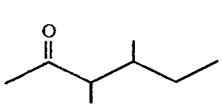 | 0.1% by weight |

This corresponds to a yield of methyl isopropyl ketone of 82.9%, based on formaldehyde employed. If the methyl isopropenyl ketone (the intermediate in the formation of methyl isopropyl ketone) is included, the yield is 89.7%. It is noteworthy that the proportion of 2,3-dimethylhexan-2-one formed, this being the self-condensation product of methyl ethyl ketone, is virtually negligible.

EXAMPLE 2

1.0 liter per hour of a mixture which consists of 82.5% of methyl ethyl ketone and 17.5% of an aqueous 30% strength formaldehyde solution was reacted at 170° C., under 30 bar $H_2$ pressure, in the apparatus, and over the catalyst, described in Example 1. The yield of methyl isopropyl ketone obtained was 77.7%, based on formaldehyde employed. If the methyl isopropenyl ketone obtained is included as a useful product, the yield is 84.1%. The proportion of 2,3-dimethyl-hexan-2-one formed under the conditions described was 0.2%.

EXAMPLE 3

0.4 liter per hour of a mixture of 68.4% of methyl ethyl ketone and 31.6% of an aqueous 30% strength formaldehyde solution was reacted, under 30 bar $H_2$ pressure, in the apparatus, and over the catalyst, described in Example 1. At a reaction temperature of 190° C., the yield of methyl isopropyl ketone was 78.9% based on formaldehyde employed. If the methyl isopropenyl ketone is included, the yield is 83.2%. Once again, the proportion of 2,3-dimethyl-hexan-2-one formed was low, namely 0.1%.

EXAMPLE 4

1.0 liter per hour of a mixture of acetone and aqueous 30% strength formaldehyde solution (the molar ratio of acetone to formaldehyde being 8:1) was reacted at 160° C. under 40 bar $H_2$ pressure in the reactor described in Example 1, over a catalyst consisting of titanium phosphate plus 0.5% of Pd. Methyl ethyl ketone was obtained in a yield of 73.3% based on formaldehyde employed. The proportion of methyl isobutyl ketone formed, this being the dimerization product of acetone, was 0.8%.

EXAMPLE 5

0.5 liter per hour of a mixture of acetophenone and a 30% strength solution of formaldehyde in isobutanol (the molar ratio of acetophenone to formaldehyde being 8:1) was reacted at 180° C., under 30 bar $H_2$ pressure, in the apparatus, and over the catalyst, described in Example 1. The yield of propiophenone obtained was 52.8%, based on formaldehyde employed.

EXAMPLE 6

0.5 liter per hour of a mixture of cyclohexanone and a 30% strength solution of formaldehyde and isobutanol (the molar ratio of cyclohexanone to formaldehyde being 6:1) was reacted, at 180° C. under a hydrogen pressure of 30 bar, in the apparatus, and over the catalyst, described in Example 1. The desired product 2-methylcyclohexanone was obtained in 45.3% yield, based on formaldehyde employed.

We claim:
1. A process for the preparation of a carbonyl compound of the general formula I

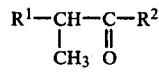

where $R^1$ and $R^2$ are straight-chain or branched alkyl of 1 to 8 carbon atoms or are aryl or aralkyl, $R^1$ may also be H and $R^1$ and $R^2$ together with the carbon atoms between them may also be members of an alicyclic ring, wherein a ketone of the general formula II

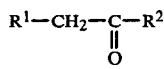

is reacted with formaldehyde at 50°–230° C. in the presence of hydrogen and of a catalyst in which the active constituents are
 (a) a phosphate of one or more of the metals zirconium, titanium, hafnium and tin or a mixture of such phosphates and
 (b) metallic palladium deposited on this phosphate (or phosphate mixture).

2. The process of claim 1, wherein said catalyst contains 0.1–5.3% by weight palladium based on said metal phosphate or metal phosphate mixture, and the molar ratio of the metallic component of said metal phosphate or metal phosphate mixture to phosphate is from 3:1 to 1:3.

3. The process of claim 1, wherein said catalyst contains 0.2–3.0% by weight palladium based on said metal phosphate or metal phosphate mixture, and the molar ratio of the metallic component of said metal phosphate or metal phosphate mixture to phosphate is from 0.6:1 to 1.7:1.

4. The process of claim 1, wherein the molar ratio of said carbonyl compound to formaldehyde is from 1:1 to 20:1.

5. The process of claim 1, wherein the molar ratio of said carbonyl compound to formaldehyde is from 1:1 to 15:1.

6. The process of claim 1, wherein the pressure of hydrogen is less than 100 bar.

7. The process of claim 1, wherein the pressure of hydrogen is from 1–50 bar.

8. The process of claims 2 or 3, wherein the molar ratio of said carbonyl compound to formaldehyde is from 1:1 to 15:1, and the pressure of hydrogen is from 1–50 bar.

9. The process of claim 8, wherein the temperature is from 70°–210° C.

* * * * *

UNITED STATES PATENT AND TRADEMARK OFFICE
CERTIFICATE OF CORRECTION

PATENT NO. : 4,374,274

DATED : February 15, 1983

INVENTOR(S) : Gerd Heilen et al.

It is certified that error appears in the above-identified patent and that said Letters Patent is hereby corrected as shown below:

On the title page Insert:

[30] -- Foreign Application Priority Data

October 12, 1979 [JP] Japan..... 2941386 --

Signed and Sealed this

Twenty-sixth Day of April 1983

|SEAL|

Attest:

GERALD J. MOSSINGHOFF

Attesting Officer       Commissioner of Patents and Trademarks